US00PP11752P2

(12) United States Plant Patent
Schuurman

(10) Patent No.: US PP11,752 P2
(45) Date of Patent: Jan. 23, 2001

(54) HYBRID TEA ROSE PLANT NAMED 'SUNLUCK'

(75) Inventor: Frank Schuurman, Auckland (NZ)

(73) Assignee: Franko Roses New Zealand Limited, Auckland (NZ)

( * ) Notice: Under 35 U.S.C. 154(b), the term of this patent shall be extended for 0 days.

(21) Appl. No.: 09/212,329

(22) Filed: Dec. 15, 1998

(51) Int. Cl.[7] ..... A01H 5/00
(52) U.S. Cl. ..... Plt./134
(58) Field of Search ..... Plt./134

(56) References Cited

U.S. PATENT DOCUMENTS

P.P. 9,116 * 4/1995 Kordes ..... Plt./135

* cited by examiner

*Primary Examiner*—Howard J. Locker
(74) *Attorney, Agent, or Firm*—Christie, Parker & Hale, LLP

(57) ABSTRACT

A bybrid tea rose plant variety producing yellow flowers of good form.

1 Drawing Sheet

BACKGROUND OF THE INVENTION

The present invention relates to a new and distinct hybrid tea rose variety (*Rosa hybrida*) which was originated by my crossing as seed parent the variety known as 'Lambada' (also known as 'Lambada', U.S. Plant Pat. No. 9,116) and as pollen parent the variety known as 'Texas'. The varietal denomination of this new rose is 'Sunluck'.

SUMMARY OF THE INVENTION

Among the novel characteristics possessed by the new variety which distinguish it from its parents and all other varieties of which I am aware are its attractive yellow flower color.

Asexual reproduction by budding of the new variety as performed in Watsonville, Calif., shows that the foregoing and other distinguishing characteristics come true to form and are established and transmitted through succeeding propagations. Other known forms of asexual reproduction may be also used.

COMPARISON WITH PARENTS

'Lambada' is an orange rose with small dull green foliage. 'Sunluck' is a golden hybrid tea with large foliage. 'Texas' is a large yellow hybrid tea with a substantial red coloring on the outer petals while 'Sunluck' is a pure golden yellow.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

The following is a detailed description of the new variety, from specimens grown in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

1. Flower: Blooms continuous under greenhouse conditions.
   - *A. Bud.*—(1) Size: About 4 to 4.5 cm in length; about 2.4 to 3 cm in width. (2) Form: Pointed. (3) Color: When sepals first divede near 9A with slight veining of near 1B at base; near 8A on edges. (4) Sepals: Outside near 146A on edges with near 144A on center; inside near 147B on edges with near 147C in center; inside covered with small hairs; acute elliptical with some leaf pointed ends, some sepals have small leafs protruding from sides; about 4.1 to 5.4 cm in length; sepals cover bud then divide and unfurl. (5) Peduncle: Length: About 7.3 to 8.5 cm. Aspect: Small prickles. Strength: Erect, sturdy. Color: Near 144A. (6) Bracts: None.
   - *B. Bloom.*—(1) Size: About 10 to 12 cm in width; about 7 to 7.5 cm in depth. (2) Borne: Singly. (3) Form: High centered at first, very nicely imbricated, petals reflex upon maturity. (4) Petalage: About 29 to 34. (5) Color: (⅓ to ½ open): Outer petals — Top surface near 14B, under surface near 13B. Inner Petals — Top surface near 14A, under surface near 13A. Base of petals —Near 15A. General tonality from a distance: Golden yellow. (6) Color (fully open): Outer petals—Top surface near 14B, under surface near 13B. Inner petals—Top surface near 14A, under surface near 13A. Base of petals: Near 15B. General tonality from a distance: Golden yellow. (7) Color Change: Fairly constant. General tonality at a distance: Golden yellow.
   - *Petals.*—(1) Texture: Thick, smooth. (2) Appearance: Inside soft velvety appearance; outside matte finish. (3) Form: Fan-shaped, rolled under at maturity. (4) Arrangement: Imbricated. (5) Petaloids: Few, 1 to 3. (6) Fragrance: Strong. (7) Lasting quality: On plant about 14 to 16 days, after cutting about 10 to 12 days. (8) Persistence: Drop cleanly.
2. Reproductive organs:
   - *A. Stamens.*—(1) Arrangement: Introse, bunched tightly around style. (2) Color: Filaments: Near 17A. Anthers: Near 17B. Pollen: Near 17B.

*B. Pistils.*—(1) Styles: Bunched, uneven, about 0.5 to 1 cm in length. (2) Stigmas: Near 1B in color.

*C. Characteristics of hips.*—Obovate, Near 25C.

3. Plant:

*A. Form.*—Very upright.

*B. Growth.*—Vigorous.

*C. Foliage.*—Compound 3 and 5 leaflets (1) Size: Large, about 9.7 to 10.3 cm by 5.3 to 6.2 cm. (2) Quantity: Abundant (3) Color: New foliage upper side near 189A with heavy veining of near 184A, underside near 189B with edging near 184B; old foliage upper side near 147A, underside near 147B with tinges of near 184B. (4) Shape: Oval. (5) Texture: Leathery. (6) Edge: Serrated. (7) Serration: Denticulate. (8) Stipules: Adnate, narrow triangular auricles facing outwards. (9) Rachis: Appears smooth, but under magnification sparse prickles. (10) Petioles: Top surface near 166A, under side near 146C. (11) Auricle: Spreading outwardly, slightly bearded margins. (12) Resistance to disease: Very resistant to blackspot, mildew and rust.

*D. Wood.*—(1) New Wood: Color near 146C, other side near 146C with shadings near 174A; bark smooth.

*E. Flower stem.*—About 80 to 100 cm.

*F. Thorns.*—Quantity: Ordinary on basal canes; few on laterals. Form: Needle shaped curving slightly downward. Color: Near 176C when young.

*G. Uniqueness.*—Attractive golden yellow rose having good petal texture, high production and long stems about 80 to 100 cm; about 160 to 200 stems per square meter per year, and outstanding holding quality of up to about 12 days.

I claim:

1. A new and distinct hybrid tea rose plant of the variety, substantially as shown and described.

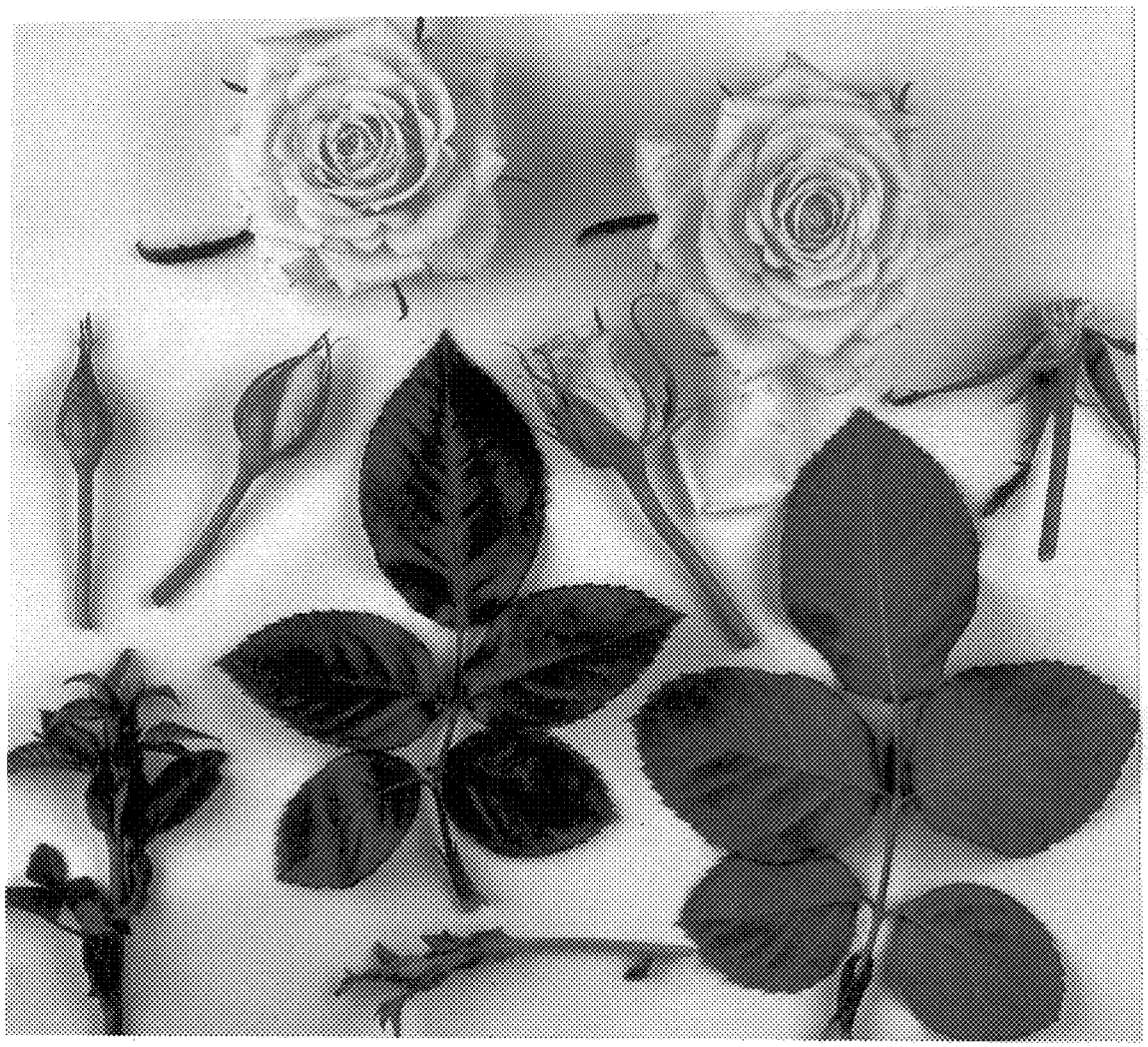

* * * * *